United States Patent
Bergmann et al.

(10) Patent No.: US 6,388,061 B1
(45) Date of Patent: May 14, 2002

(54) MONOMERIC BUILDING BLOCKS FOR LABELING PEPTIDE NUCLEIC ACIDS

(75) Inventors: Frank Bergmann, Iffeldorf; Rupert Herrmann; Christoph Seidel, both of Weilheim, all of (DE); Troels Koch, Kopenhagen S. (DK)

(73) Assignee: Dako A/S, Glostrup (DK)

( * ) Notice: Subject to any disclaimer, the term of this patent is extended or adjusted under 35 U.S.C. 154(b) by 0 days.

(21) Appl. No.: 09/381,301

(22) PCT Filed: Mar. 24, 1998

(86) PCT No.: PCT/EP98/01723

§ 371 Date: Jan. 14, 2000

§ 102(e) Date: Jan. 14, 2000

(87) PCT Pub. No.: WO98/42735

PCT Pub. Date: Oct. 1, 1998

(30) Foreign Application Priority Data

Mar. 25, 1997 (DE) .......................................... 197 12 530

(51) Int. Cl.[7] .................... C07H 19/00; C07H 21/00; C07H 21/02; C07H 21/04; C12Q 1/68
(52) U.S. Cl. .................... 536/23.1; 435/6; 536/22.1; 536/24.1; 536/25.3; 514/1; 514/44
(58) Field of Search .......................... 435/6; 536/22.1, 536/23.1, 24.3, 25.3; 514/1, 44

(56) References Cited

U.S. PATENT DOCUMENTS

6,071,699 A * 6/2000 Meade et al. .................. 435/6

FOREIGN PATENT DOCUMENTS

| DE | 44 08 533 | 9/1995 |
| EP | 0 781 853 | 7/1997 |
| GB | 2 284 208 | 5/1995 |
| WO | 95 16202 | 6/1995 |
| WO | 96 11205 | 4/1996 |

OTHER PUBLICATIONS

Haaima et al, "Peptide nucleic acids (PNAs) containing thymine monomers derived from chiral amino acids: hybridization and solubility properties of D–lysine PNA", Angew. Chem., Int. Ed. Engl. (1996) 35(17) 1939–1941, Sep. 20, 1996.

* cited by examiner

Primary Examiner—Jezia Riley
(74) Attorney, Agent, or Firm—Arent Fox Kintner Plotkin & Kahn

(57) ABSTRACT

The invention relates to novel monomeric building blocks for labeling peptide nucleic acids and similarly constructed nucleic acid-binding oligomers possessing groups which are coupled to a nitrogen base and/or to the peptide backbone of the peptide nucleic acid. The invention furthermore relates to peptide nucleic acids which contain at least one labelled monomeric building block.

35 Claims, 4 Drawing Sheets

D-Lys-THYMINE PNA MONOMER

PNA MONOMERS

BASE= N⁶-Z-Ade, N²-Z-Gua, N⁴-Z-Cyt, Thy

LINKER

Ado

LABEL

Ru(bpy)$_3$-ACID (Ru)

Biotin (Bio)

Ru(bpy)$_3$-Lys (Ru-Lys)

RESIN

MBHA-Gly

MONOMERIC BUILDING BLOCKS FOR LABELING PEPTIDE NUCLEIC ACIDS

DESCRIPTION

Figure 1:
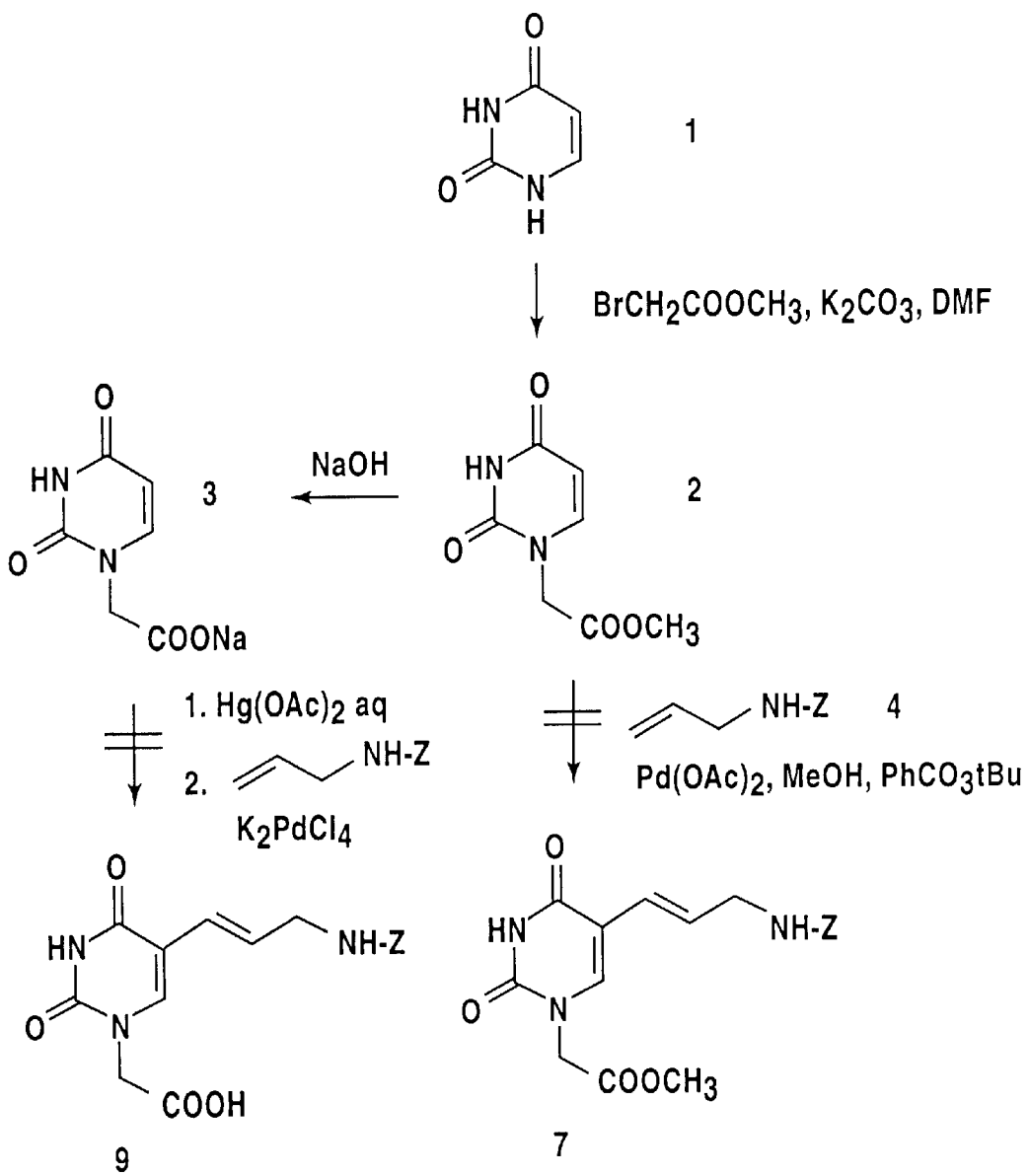

The invention relates to novel monomeric building blocks for labeling peptide nucleic acids and similarly constructed nucleic acid-binding oligomers possessing groups which are coupled to a nitrogen base and/or to the peptide backbone of the peptide nucleic acid. The invention furthermore relates to peptide nucleic acids which contain at least one labelled monomeric building block.

The chemical insertion of labeling groups, e.g. reporter molecules, into nucleic acids is of great importance for a large number of applications. The requirement here is for couplable groups, e.g. amino groups, to be incorporated into the nucleic acid in a specific manner. Specially modified monomeric nucleotide building blocks, which are compatible with the strategy for synthesizing nucleic acids which is subsequently employed, are prepared for this purpose. Thus, trifluoroacetyl-protected or Fmoc-protected aminoalkyloxy-phosphoramidites are, for example, used for 5'-end-labeling in nucleic acid chemistry (cf., e.g., EP-A-224 578, Coull et al., Tetrahedron Lett. 27 (1986), 3991–3994). Phosphoramidites which contain a trifluoroacetyl-protected or Fmoc-protected amino acid group and a DMTr ether have been used for labeling within a nucleic acid molecule, with it being possible for the parent substances to be of non-nucleotide (EP-A-0 313 219, Nelson et al., Nucleic Acids Res. 17 (1989), 7179–7186) or nucleotide (Ruth, DNA 4 (1985), 93, WO 84/03285) nature. In the case of a nucleotide parent substance, particular positions in the nitrogen base or the sugar are suitable for coupling reporter molecules (cf., e.g., Ruth (1991) Oligodeoxynucleotides with reporter groups attached to the base, in: Oligonucleotides and Analogs; A Practical Approach (F. Eckstein, HRSG), Oxford University Press, Oxford, UK, pp. 255–282 and Manoharan et al., Tetrahedron Lett. 36 (1995) 3647–3650).

Corresponding nucleoside triphosphates which are modified at the level of the nitrogen base or the ribose and which are suitable for enzymically synthesizing a nucleic acid are likewise known (EP-A-0063 879, EP-A-0286 898).

The functional groups which are able to couple reporter molecules can be blocked by a suitable protecting group such that the reporter group can only be coupled after the protecting group has been removed from the synthesized nucleic acid by means of so-called post-labeling. However, a reporter molecule can also be directly coupled onto the functional group provided that it is stable under the conditions pertaining during nucleic acid synthesis and protecting group removal. An amino side group which is able to couple reporter molecules can otherwise also be introduced at internucleotide phosphate groups, with the resulting oligonucleotide phosphite triesters or H-phosphonate being oxidized to the corresponding phosphoramidate using a mono-protected diamine (WO 92/08728 and Agrawal et al., Nucleic Acids Res. 18 (1990), 5419).

In the case of the hybridization of nucleic acids which are coupled to reporter molecules within the strand, the melting temperature, Tm, is generally found to be lower after a complementary nucleic acid counterstrand has been hybridized on. In some cases, this lowering of the melting temperature can lead to problems with regard to the specificity and sensitivity of nucleic acid hybridization methods.

As a result of the higher affinity and selectivity, as compared with customary nucleic acids, in their base pairing with a complementary nucleic acid counterstrand, peptide nucleic acids (PNAs) are gaining ever increasing importance for carrying out hybridization reactions (Egholm et al., J. Am. Chem. Soc. 114 (1992), 1895–1897, WO 92/20 702 and WO 92/20 703). In the PNAs, the sugar phosphate backbone of the nucleic acids is replaced with a peptide backbone, e.g. a 2-aminoethylglycine backbone. The nitrogen bases are coupled on at their central nitrogen atom, e.g. by way of a methylenecarbonyl group. The synthesis of a PNA therefore differs appreciably from that of a DNA since different protecting groups and coupling schemes are required. To date, functional groups for further derivatizations, e.g. for inserting reporter molecules, have been introduced at the N terminus of the last PNA building block either directly or after one or more ω-amino acids have been additionally coupled on. It has also been possible to insert functionalizable groups terminally by incorporating lysine residues at the C terminus and at the N terminus.

Since only a limited number of reporter molecules can be inserted into PNA by means of this terminal labeling, there is a great need for alternative methods for inserting labeling groups into PNA.

The present invention achieves this object by providing novel monomeric building blocks for PNA synthesis, which building blocks allow labeling groups to be inserted within the PNA molecule strand, with the labeling group being coupled to a nitrogen base and/or to a peptide backbone.

Surprisingly, it was observed, in this connection, that when PNAs are labeled on their nitrogen bases and on their peptide backbone there is then either an increase in the melting temperature of hybrids with a nucleic acid as compared with hybrids containing unlabeled PNA strands or else the destabilization is at least weaker than in the case of a corresponding DNA-DNA hybrid which contains a labeled DNA strand. This surprising increase in the melting point leads to an increased specificity in hybridization reactions and enables more stringent washing conditions and/or shorter probes to be used in detection methods.

A first embodiment of the present invention relates to monomeric building blocks for synthesizing nucleic acid-binding peptide oligomers which carry a labeling group, or a group which is able to couple with a labeling group, on the nitrogen base. Such monomers are preferably depicted by compounds of the formula (I):

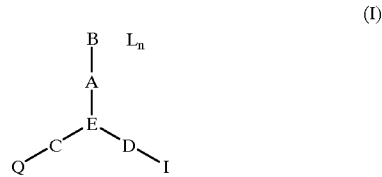

in which:
B is a natural or unnatural nitrogen base which optionally carries a protecting group,
L is a labeling group which is preferably selected from signal-emitting groups, intercalators and pharmaceutically active groups or a group which is able to couple with a labeling group and which optionally carries a protecting group,
A, C and D are in each case, independently of each other, chemical bonds or organic radicals,
E is a group which is selected from N, $R^1N^+$ or CH, where $R^1$ is an organic radical or hydrogen,
Q is a group $NR^2Y$, where $R^2$ is an organic radical or hydrogen, and Y is a protecting group or a carrier, I is a group which is selected from COX, CSX, SOX or SO$_2$X, where X is OH, SH, OM, SM or a protecting group, and M is a cation, preferably a metal cation or an ammonium cation, and n is an integer from 1 to 3, preferably 1.

A, C and D are preferably C$_1$–C$_{10}$-alkylene, alkenylene or alkynylene radicals which can optionally carry heteroatoms such as O, N, P or halogen and/or substituents.

A is particularly preferably a —(CH$_2$)$_l$—CO— radical, where l is an integer from 0 to 5. A is most preferably a —CH$_2$CO— radical. C is particularly preferably a —(CH$_2$)$_k$—CHR'— radical, where k is an integer from 0 to 5 and R' is hydrogen or the side chain of a naturally occurring amino acid. C is most preferably a —(CH$_2$)$_2$— radical. D is particularly preferably a (CH$_2$)$_m$—CHR"— radical, where m is an integer from 0 to 5 and R is hydrogen or the side chain of a naturally occurring amino acid. D Is most preferably a —CH$_2$— radical. Alternatively, A and B or A and D can also be bridged with each other, i.e. form a common ring structure.

In another aspect, the present invention relates to monomeric building blocks for synthesizing nucliec acid-binding peptide oligomers which contain at least one signal-emitting group on the peptide backbone. These monomeric building blocks are preferably compounds of the formula (II):

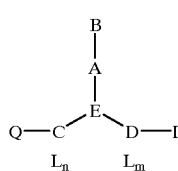

(II)

in which:

B, A, C, D, E, Q and I are defined as in the case of the (I) compounds,

L is a labeling group which is preferably selected from signal-emitting groups, intercalators and pharmaceutically active groups, and n and m are 0 or 1 to 3, with the proviso that the sum of n+m is not 0. n and m are preferably 0 or 1.

In the compounds of the formula (II), the group L is preferably a substituent of D. Particularly preferably, D is a group —CH(R'—L), where R' is an organic radical as previously defined. R' is most preferably the radical of the side chain of a naturally occurring amino acid or of the corresponding enantiomeric compound, e.g. lysine. The asymmetric C atom of the group —CH(R'—L) preferably has the D configuration.

The nitrogen base of the (I) and (II) compounds is any arbitrary natural or unnatural nitrogen base, with all the nitrogen bases which are able to hybridize with a complementary natural nitrogen base on a DNA or RNA molecule being suitable in principle. The nitrogen base B is preferably selected from thymine, uracil, cytosine, adenine, guanine, hypoxanthine, purine, 7-deazapurine, 2,4-diaminopurine, 2,6-diaminopurine, 7-deazaguanine, pseudouracil, pseudocytosine, pseudoisocytosine, N$^4$,N$^4$-ethanocytosine, N$^6$,N$^6$-ethano-2,6-diaminopurine, 5-(C$_3$–C$_6$)-alkynylcytosine, 5-fluoro-uracil or 2-hydroxy-5-methyl-4-triazolopyrimidine, with the nitrogen base optionally carrying a protecting group.

Since numerous variants of the basic structure of PNA monomers are known in the state of the art, the radicals A, C, D, E, Q and I can assume a large number of known meanings. The reader is particularly referred, with regard to the meaning of these radicals, to the documents WO 92/20 702, WO 92/20 703, DE-A-43 31 012, DE-A-44 08 531, DE-A-44 08 533, DE-A-44 25 311 and EP-A-0 739 898. The relevant passages in these documents relating to the meaning of the abovementioned radicals are hereby incorporated into the present description by reference.

The nitrogen base B preferably carries one or more protecting groups, in particular on exocyclic amino functions.

A protecting group according to the present invention is a chemical group which prevents the functional group to which it is bonded from participating in an undesirable chemical reaction. The protecting group can be removed from this functional group without destroying it.

Examples of suitable protecting groups are base-labile protecting groups such as 9-fluoroenylmethoxycarbonyl (Fmoc), 2,2-[bis(4-nitrophenyl)]ethoxycarbonyl (Bnpeoc), 2-(2,4-dinitrophenyl)ethoxycarbonyl (Dnpeoc), 2-(4-nitrophenyl)ethyloxycarbonyl, 1-(4,4-dimethyl-2,6-dioxocyclohexylidene)ethyl (Dde) and 2-methylsulfonylethyloxycarbonyl (Msc). Of these protecting groups, particular preference is given to Fmoc. Furthermore, acid-labile protecting groups of the urethane type, such as tert-butyloxycarbonyl (Boc) and 4-methoxybenzyloxycarbonyl (Moz), or of the trityl type, such as triphenylmethyl (Trt), (4-methoxyphenyl)diphenylmethyl (Mmt), (4-methylphenyl)diphenylmethyl (Mtt) and di-(4-methoxyphenyl)phenylmethyl (Dmt), are also suitable. Of these protecting groups, particular preference is given to Poc, Trt, Mmt, Mtt and Dmt. Finally, protecting groups of the acyl type, such as benzoyl (Z), isobutyryl, acetyl, phenoxyacetyl, 4-(t-butyl)-benzoyl and 4-(t-butyl)-phenoxyacetyl-4-(methoxy)benzoyl, are also suitable. It is expedient to use those protecting groups which are compatible with the proposed strategy of oligomer synthesis.

In compounds of the formula (I), the group L is coupled to the nitrogen base B. The preferred coupling positions are as follows: when the nitrogen base is a pyrimidine base, (C, T, U or an unnatural derivative thereof), the group L may preferably be bonded to the C-5 position. When the nitrogen base is a cytosine or a derivative thereof, the group L may preferably be bonded to the N-4 position. When the nitrogen base is a purine base (A, G or a derivative thereof), the group L may preferably be bonded to the C-8 position. When the nitrogen base is adenine or a derivative thereof, the group L may preferably be bonded to the N-6 position. When the nitrogen base is a purine base, the group L may preferably be bonded to the N-2 position. When the nitrogen base is a 7-diazapurine, the group L may preferably be bonded to the C-7 position. Particular preference is given to the nitrogen base being a pyrimidine base and to the group L being bonded to the C-5 position.

The group L is a group which is preferably selected from signal-emitting groups, intercalators and pharmaceutically active groups or a group which is able to couple with one of the previously mentioned groups. The group L may carry one or more protecting groups insofar as this is necessary for preventing undesirable reactions under the conditions pertaining during the PNA synthesis. The group L is preferably coupled to the nitrogen base B by way of a bond which is stable under conditions in association with which the intermediate protecting groups which are employed for the given synthesis strategy are eliminated. In particular, L is preferably not an exocyclic amino function which is directly protected by a base-labile protecting group. In the present invention, an exocyclic amino function is understood as being an amino function which is located directly (i.e. not by way of a linker) on the heterocycle.

The group L is preferably a signal-emitting group or a reporter molecule. All the previously known signal-emitting groups for polypeptides and nucleotides, in particular non-radioactive signal-emitting groups, are suitable for this purpose. Chromogens (fluorescent or luminescent groups and dyes), enzymes, NMR-active groups or metal particles, haptens, e.g. digoxigenin, or biotin and derivatives thereof which are able to bind to streptavidin or avidin, are examples of such groups. Furthermore, the labeling group can also be a photoactivatable crosslinking group, e.g. an azido or an azirine group. Metal chelates which can be detected by electrochemoluminescence are particularly preferred signal-emitting groups, with particular preference being given to ruthenium chelates, e.g. a ruthenium (bispyridyl)$_3^{2+}$ chelate. Suitable ruthenium labeling groups are described, for example, in EP-A-0580 979, WO 90/053 01, WO 90/11 511 and WO 92/14 138. These documents are hereby incorporated into the present description by reference.

Furthermore, the group L can also be an intercalator which can intercalate into a PNA-nucleic acid hybrid and in this way enable it to be detected, where appropriate. Examples of suitable intercalators are thiazole orange, ethidium bromide and propidium iodide.

The group L can furthermore be a pharmaceutically active group, e.g. an RNA-cleaving group such as an imidazole-containing residue (cf. WO 93/17 7117, DE-A-44 25 311, WO 96/07 667, or a group which is able to improve the pharmacodynamic or pharmacokinetic properties (WO 94/068 15). These documents are hereby incorporated into the present description by reference.

In the case of the compounds of the formulae (I) and (II), labeling groups can, provided they are compatible with the conditions prevailing in association with the given synthesis strategy, be introduced into the monomeric building block before the nucleic acid-binding oligomers are synthesized. Where appropriate, compatibility can be achieved and/or improved by inserting appropriate groups on functional protecting groups, such as amino or OH groups, in the labeling groups. Examples of suitable groups which are stable during oligomer synthesis are luminescent metal chelates, such as ruthenium (bipyridyl)$_3$, biotin or fluorescein.

On the other hand, the group L can also be a radical which is able to couple to a labeling group. Examples of suitable radicals are reactive groups, such as amino groups or active esters, which are preferably connected to the nitrogen base or the peptide backbone by way of suitable linkers. In this case, L in compounds of the formula (I) then preferably has the structure —R'—NHY, where R' is a $C_2$–$C_{10}$ alkylene, alkenylene or alkynylene radical which optionally contains heteroatoms, and Y is a protecting group. R' is particularly preferably a —CH=CH—CH$_2$— group.

The novel compounds of the formulae (I) and (II) can be employed as monomeric building blocks in the synthesis of nucleic acid-binding peptide oligomers. Nucleic acid-binding peptide oligomers are compounds which are composed of several monomeric building blocks, with the building blocks being linked at least partially by way of peptide bonds or other acid amide bonds (e.g. CONH, CONR$^2$, CSNH, CSNR$^2$, SONH, SONR$^2$, SO$_2$NH or SO$_2$NR$^2$, where R$^2$ is defined as previously). In addition, these oligomers can bind to nucleic acids by way of base pairing. Such base pairing is usually effected by means of hydrogen bonds between complementary nitrogen bases. In principle, nucleic acid-binding oligomers are able to bind to nucleic acids in two ways. In the first case, a strand of the nucleic acid-binding oligomer binds to a selected region of a single-stranded nucleic acid, with a double strand or duplex being formed. In the second case, two molecules of the nucleic acid-binding oligomer can form a complex with the selected region of a nucleic acid, with a triple helix strand or triplex being formed. Peptide nucleic acids as known from WO 92/20 702 are examples of nucleic acid-binding oligomers. However, the present invention does not only cover PNAs having identical, repeating backbone groups; it also covers nucleic acid-binding oligomers in which the backbone consists of different monomeric subunits, as are described in WO 95/14 706. It furthermore covers compounds according to EP-A-0 627 677, which discloses mixed structures composed of peptide-bound monomers and oligonucleotide subunits. It also covers compounds as disclosed in WO 96/20 212 and EP-A-0 700 928. The abovementioned documents are hereby incorporated into the description by reference.

Nucleic acid-binding oligomers which are particularly preferred are peptide nucleic acids according to formula (III):

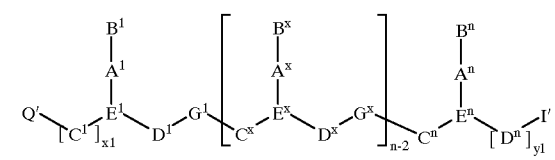

(III)

in which n is an integer of at least 3, x is an integer from 2 to n−1, each of the groups $B^1$ to $B^n$ is a nitrogen base as previously defined, each of the groups $C_1$–$C^n$ has the meaning $(CR^6R^7)_y$, preferably $CR^6R^7$, $CHR^6CHR^7$ or $CR^6R^7CH_2$, where $R^6$ is hydrogen and $R^7$ is selected from the group consisting of the side chains of naturally occurring alpha-amino acids, or $R^6$ and $R^7$ are independently selected from the group consisting of hydrogen, $C_1$–$C_6$-alkyl, aryl, aralkyl, heteroaryl, hydroxyl, $C_1$–$C_6$-alkoxy, $C_1$–$C_6$-alkylthio, $NR^3R^4$ and $SR^5$, where $R^3$ and $R^4$ are as defined below and $R^5$ is hydrogen, $C_1$–$C_6$-alkyl or $C_1$–$C_6$-alkyl which is substituted by hydroxyl, $C_1$–$C_6$-alkoxy or $C_1$–$C_6$-alkylthio, or $R^6$ and $R^7$ together form an alicyclic system or heterocyclic system, or $C_1$–$C^n$ is CO, CS or $CNR^3$;

each of the radicals $D^1$–$D^n$ has the meaning $(CR^6R^7)_2$, preferably $CR^6R^7$, $CHR^6CHR^7$ or $CH^2CR^6CR^7$, where $R^6$ and $R^7$ are as defined before, and y and z are integers of from 0 to 10, where the sum of y+z is at least 2, preferably more than 2 but not more than 10;

each of the radicals $G^1$–$G^{n-1}$ has the meaning —$NR^3CO$—, —$NR^3CS$—, —$NR^3$—$SO$— or —$NR^3SO_2$ in any orientation, where $R^3$ is as defined below;

each of the radicals $A^1$–$A^n$ and $E^1$–$E^n$ is selected such that:

(a) $A^1$–$A^n$ is a group of the formula (IIIa) (IIIb), (IIIc) or (IIId), and $E^1$–$E^n$ is N or $R^3N'$, or (b) $A^1$–$A^n$ is a group of the formula (IIId), and $E^1$–$E^n$ is CH:

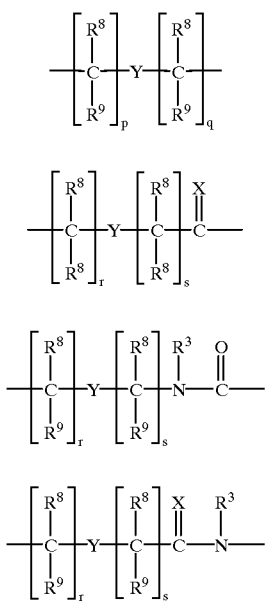

(IIIa)
(IIIb)
(IIIc)
(IIId)

in which:

X is O, S, Se, NR³, CH₂ or C(CH₃)₂,

Y is a single bond, O, S or NR⁴, p and q are in each case an integer of from 0 to 5, where the sum p+q is preferably not larger than 5;

r and s are in each case integers of from 0 to 5, where the sum r+s is preferably not larger than 5;

each of the radicals $R^8$ and $R^9$ is selected independently from the group consisting of hydrogen, hydroxyl, amine, halogen, $C_1$–$C_4$-alkoxy, $C_1$–$C_4$-alkylthio and optionally substituted $C_1$–$C_4$-alkyl, where the substituents are preferably selected from hydroxyl, $C_1$–$C_4$-alkoxy or $C_1$–$C_4$-alkylthio groups;

each of the radicals $R^3$ and $R^4$ is selected independently from the group consisting of hydrogen, $C_1$–$C_4$-alkyl which is optionally substituted by hydroxyl or $C_1$–$C_4$-alkoxy or $C_1$–$C_4$-alkylthio, hydroxyl, $C_1$–$C_6$-alkoxy, $C_1$–$C_6$-alkylthio and amine;

Q' and I' are selected independently from the group consisting of NH₂, CONH₂, COOH, hydrogen, $C_1$–$C_6$-alkyl, O($C_1$–$C_6$)-alkyl, an amine which is blocked by a protecting group, labeling groups, intercalators, chelators, peptides, proteins, carbohydrates, lipids, steroids, nucleosides, nucleotides, nucleosidediphosphates, nucleosidetriphosphates, oligonucleotides, including oligoribonucleotides and oligodeoxyribonucleotides, oligonucleosides and soluble and insoluble polymers and also nucleic acid-binding groups, and x1 and y1 is in each case an integer of from 0 to 10, with the compound being such that a group L as previously defined is present at at least one nitrogen base and/or at a position in the peptide backbone.

Most preferably, the nucleic acid-binding oligomers comprise at least one monomeric subunit of the general formula (IV):

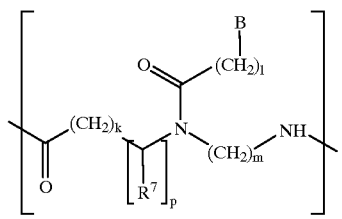

in which:

B is a nitrogen base as previously defined, k, l and m are, independently, an integer from 0 to 5, p is 0 or 1, and $R^7$ is selected from the group consisting of hydrogen and the side chains of naturally occurring alpha-amino acids.

The synthesis of PNA building blocks according to the invention is described using as an example the nitrogen base thymidine, into which an allylamino group, which is able to couple to other groups, e.g. labeling groups such as Ru(bipyridyl)₃, was introduced.

Figure 2:
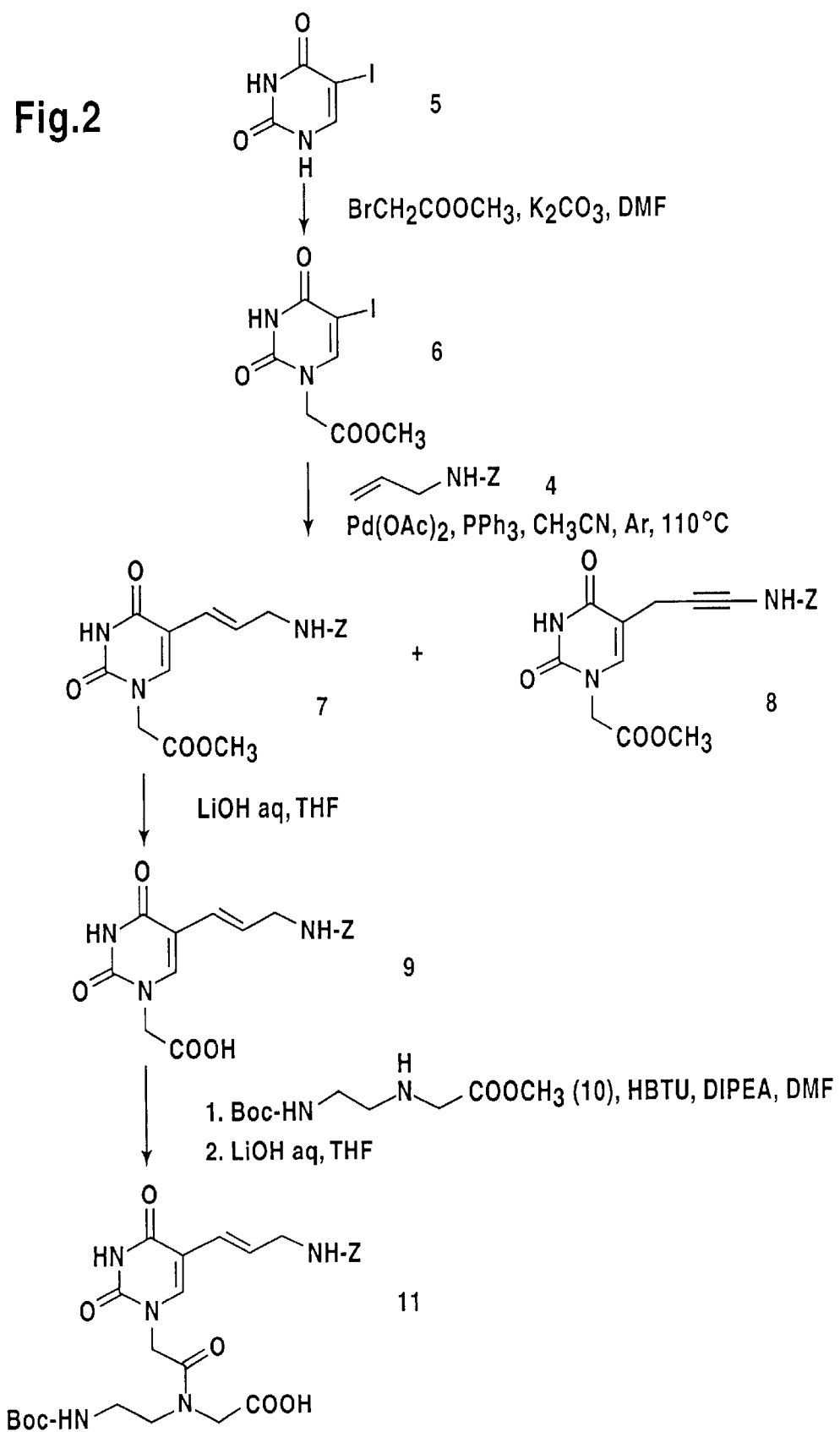

It turned out to be difficult to synthesize the thymine PNA building block which was amino-modified in the C-5 position. Two different synthesis strategies are depicted in FIG. 1 and FIG. 2. As seen in FIG. 1, methyl uracil-1-acetate (2) was prepared from uracil (1) and methyl bromoacetate, with the methyl uracil-1-acetate then being saponified with sodium hydroxide solution to give the corresponding sodium salt (3). An attempt to react 2 with Z-protected allylamine 4 by way of an oxidative coupling using Pd(OAc)₂ and t-butyl perbenzoate in accordance with the method of Hirota et al., (Synthesis 1987, 495–496), in which the reaction of uracil derivatives and uridine derivatives is described, was not successful. The most usual method in nucleic acid chemistry, i.e. C—C linking at the C-5 position by means of the direct mercurization of unprotected 2'-deoxyuridine or 2'-deoxycytidine and subsequent alkylation in the presence of olefins (Bergstrom et al., J. Carbohydrates, Nucleosides, Nucleotides 4 (1977), 257; Bergstrom et al., J. Am. Chem. Soc. 98 (1976) 1587; Cook et al., Nucleic Acids Res. 16 (1988), 4077), was not successful either.

Astoundingly, as can be seen from FIG. 2, it was the use of a modification of the Heck reaction (Heck, J. Am. Chem. Soc. 90 (1968), 5518), of all possible options, which led to the desired C—C linkage. 5-Iodouracil (5) was first of all alkylated with methyl bromoacetate to give methyl 5-iodouracil-1-acetate (6). The Heck reaction of 6 with Z-protected allylamine in the presence of Pd(OAc)₂ and triphenylphosphine in absolute acetonitrile was carried out with the exclusion of air and at a superelevated temperature (bath temperature of 110° C.), and yielded the compound (7) together with a small portion of the oxidized byproduct (8). The methyl ester (7) was then hydrolyzed to give the free acid (9), which was reacted with methyl 2-Boc-aminoethylglycine (10) in analogy with the method of Dueholm et al., (J. Org. Chem. 59 (1994), 5767). The desired amino-modified thymine PNA building block (11) was obtained after the ester had been subjected to alkaline hydrolysis.

The Z-protected D-Lys-thymine building block 12, which carries a couplable group on the peptide backbone (FIG. 3), is a known compound which has been used up to now for preparing PNA sequences whose solubility is improved.

The PNA was synthesized on an ABI433A peptide synthesizer in the manner described in T. Koch et al., Automated PNA Synthesis, Int. J. Peptide Protein Res., in press. The couplable components, the Boc/Z PNA standard monomers, the Ado linker, the labeling groups Ru(bpy)$_3$-acid, Ru(bpy)$_3$-Lys and biotin, and also the Boc-Gly-derivatized MBHA resin which were used are depicted in FIG. 4. The monomeric building blocks 11 (FIG. 2) and 12 (FIG. 3) were incorporated for labeling within the PNA strand. The PNA oligomers were purified by means of RP18 HPLC. PNA molecules into which the building blocks 11 or 12 had been incorporated were subsequently labelled with Ru(bpy)$_3$-OSu in DMSO and aqueous 0.1 M NaHCO$_3$.

The novel nucleic acid-binding oligomers can, of course, be synthesized in a variety of ways. Thus, a Boc/Z protecting group strategy is used in the examples of the present application, i.e. the intermediate protecting group for the PNA monomeric building blocks is Boc (elimination with trifluoroacetic acid), and the nitrogen bases are protected with Z(benzyloxycarbonyl; elimination using a trifluoromethanesulfonic acid/trifluoroacetic acid mixture). When this synthesis strategy is used, the amino groups which are present on the monomers which have been modified in accordance with the invention can also be protected with Z.

Another synthesis strategy is described in DE-A-44 08 531. This strategy uses weakly acid-labile intermediate protecting groups in the PNA monomer, in particular monomethoxytrityl. The amino groups in the nitrogen bases are protected with protecting groups which are compatible with weak acids, e.g. acyl protecting groups (benzoyl, isobutyryl, acetyl, etc.). When this strategy is used, additional amino acids which are introduced by means of the novel modification should be protected with trifluoroacetyl or Fmoc.

The synthesis strategy described in DE-A-44 08 533 uses base-labile intermediate amino protecting groups for the PNA synthesis, in particular Fmoc. The nitrogen bases are protected with base-compatible protecting groups, e.g. monomethoxytrityl, Boc, etc. The additional amino group, which is introduced by means of the novel modification and which has to be protected permanently during the synthesis, can be protected with monomethoxytrityl or Boc in this case too.

The invention furthermore relates to a nucleic acid-binding peptide oligomer which contains at least one monomeric building block which contains a labeling group which is coupled to a nitrogen base and/or to the peptide backbone. Preferably, the nucleic acid-binding oligomer contains at least one monomeric building block which is selected from compounds from the formulae (I) and (II). It is furthermore preferred that, when the novel oligomer hybridizes with a complementary nucleic acid, (1) the resulting hybrid, which can be a double strand or a triple strand, should have a higher melting point than a hybrid which contains an oligomer which possesses the same sequence but which lacks a labeling group, or (2) there should be weaker destabilization in a PNA-nucleic acid hybrid than in a nucleic acid-nucleic acid hybrid.

The novel oligomer can contain several identical or different labeling groups and, over and above this, can additionally be coupled to other identical or different labeling groups at the N terminus and the C terminus. Particular preference is given to the novel oligomer being a peptide nucleic acid and having a structure of the general formula (III), as previously defined. The PNA preferably contains at least one monomeric building block of the general formula (IV), as previously defined.

The novel nucleic acid-binding oligomers are employed for hybridizing to nucleic acids. Suitable methods in this context are, on the one hand, those for detecting and/or isolating nucleic acids, e.g. diagnostic detection methods. On the other hand, the novel oligomers can, in particular when L is a pharmaceutically active group, also be employed in therapeutic methods, e.g. as antisense molecules.

The invention also relates to reagents and reagent kits for hybridizing with nucleic acids, which kits contain a novel nucleic acid-binding oligomer in addition to other test components.

The invention will also be clarified by the sequence listings, figures and examples which follow.

Figure 3:
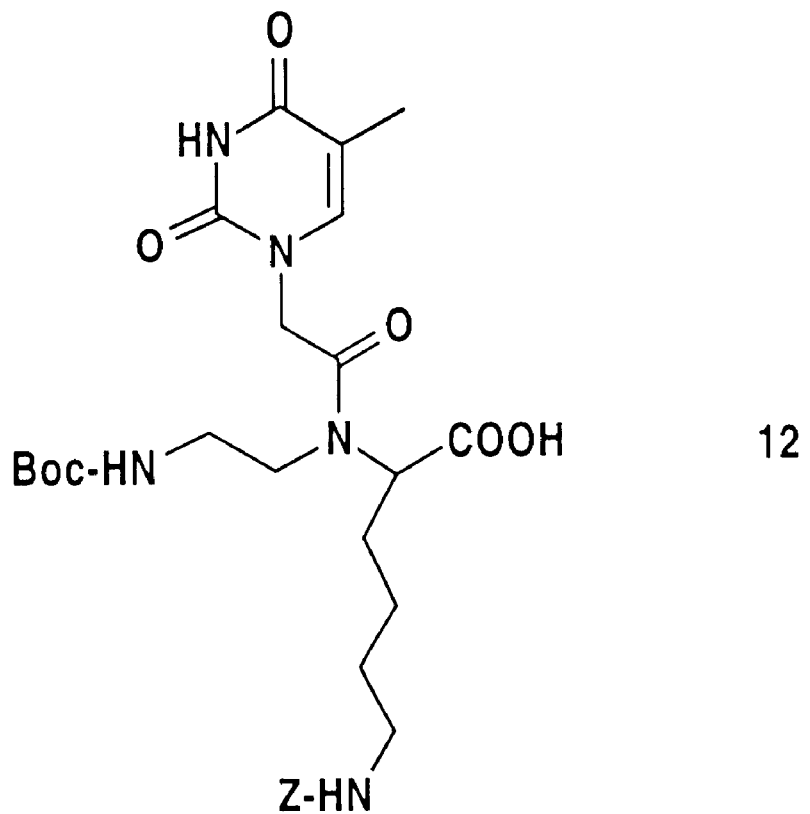
Figure 4:
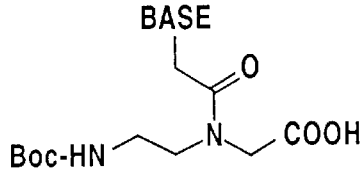
Figure 4:
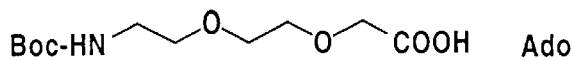
Figure 4:
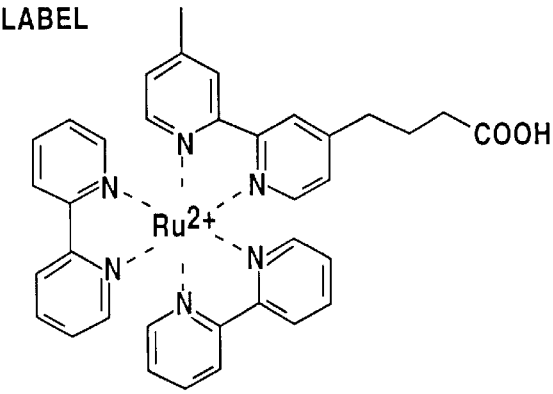
Figure 4:
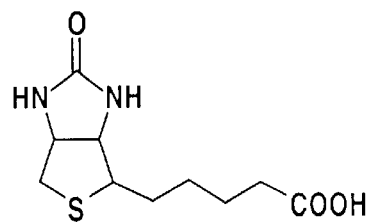
Figure 4:
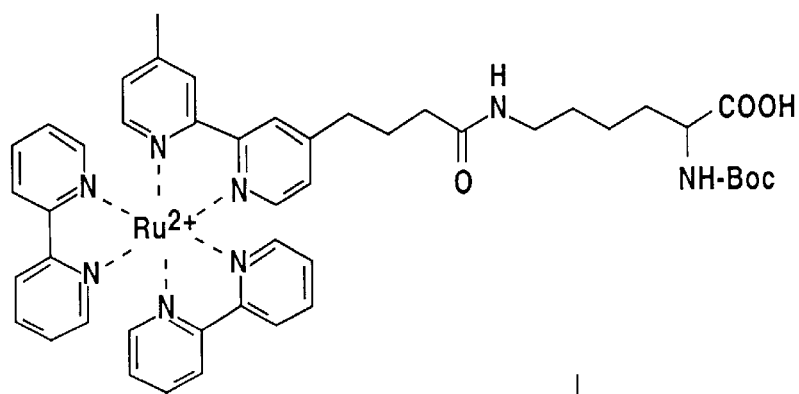
Figure 4:
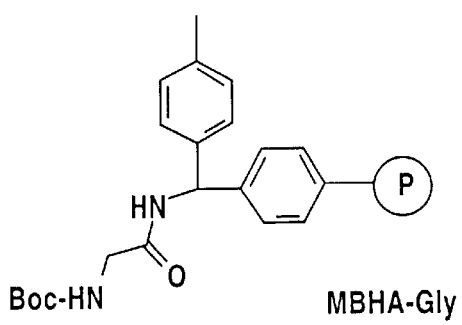

SEQ ID NO. 1: shows the nucleotide sequence of a Chlamydia probe,

SEQ ID NO. 2: shows the nucleotide sequence of a reference or counterstrand probe to the sequence shown in SEQ ID NO. 1, FIG. 1 shows, in diagram form, unsuccessful synthesis strategies for preparing the novel monomeric building blocks, FIG. 2 shows, in diagram form, a successful synthesis strategy for preparing the novel monomeric building blocks (e.g. 11), FIG. 3 shows the structure of a PNA monomer (12) which is suitable for introducing labeling groups on the peptide backbone, and FIG. 4 shows the structures of PNA monomers, linkers, labeling groups and a synthesis support resin.

EXAMPLE 1

Preparation of Methyl 5-iodouracil-1-acetate (Compound 6)

6 g of 5-iodouracil (Aldrich) are dissolved in 75 ml of absolute DMF. 3.48 g of potassium carbonate and 2.4 ml of methyl bromoacetate (Merck) are added to this solution. The mixture is stirred at room temperature overnight under an argon atmosphere. The mixture is filtered and the filtrate is concentrated to dryness in vacuo. The residue is taken up in 60 ml of water and 10 ml of 2 M hydrochloric acid and this mixture is stirred vigorously at 0° C. for 1 hour. A colorless precipitate sediments out. This precipitate is filtered off with suction and washed with water until neutral. The colorless solid is dried over phosphorus pentoxide in a desiccator.

Yield: 7.3 g (93%); M.p.: 183–184° C.; $R_f$=0.51 (silica gel; dichloromethane/methanol 100:6); $^1$H NMR (d$_6$-DMSO, ppm): 11.80 (sb, 1H, NH), 8.21 (s, 1H H—C(6)), 4.53 (s, 2H, CH$_2$), 3.70 (s, 2H, OCH$_3$).

EXAMPLE 2

Preparation of N-benzyloxycarbonylallylamine (Compound 4)

10.4 ml of allylamine and 19 ml of triethylamine are dissolved in 50 ml of absolute toluene. A 50% solution of benzyl chloroformate in toluene (46.8 ml) is added dropwise to the solution, which has been cooled in an icebath, while stirring. The mixture is stirred at room temperature for a further 1 hour in order to complete the reaction. A precipitate which has formed is filtered off. After that, the filtrate is concentrated and dried to constant weight under high vacuum (70° C., 0.5 mbar).

Yield: 19.8 g (74%) $R_f$=0.79 (silica gel, petroleum ether/ ethyl acetate 1:1) $^1$H NMR (d$_6$-DMSO, ppm): 7.49–7.08 (m, 5H, phenyl), 6.01–5.64 (m, 1H, =CH(allyl)), 5.23–4.57 (m, 3H, =CH$_2$ (allyl), NH), 5.11 (s, 2H, CH$_2$ (benzyl)), 3.74–3.60 (m, 2H, CH$_2$N)

EXAMPLE 3

Preparation of Methyl 5-(N-benzyloxycarbonylaminoallyl)uracil-1-acetate (Compound 7)

1 g of methyl 5-iodouracil-1-acetate is coevaporated twice with 20 ml of absolute acetonitrile on each occasion and aerated with argon. After that, 1.2 g of N-Z-allylamine, 80 mg of palladium(II) acetate, 0.18 g of triphenylphosphine, 0.9 ml of triethlylamine and 40 ml of absolute acetonitrile are added. The reaction mixture is stirred vigorously for 100 hours under an argon atmosphere and at an oilbath temperature of 115° C. A metal mirror is formed. After cooling, hydrogen sulfide is passed into the solution and the black precipitate which has formed is filtered off through a Seitz filter. The filtrate is then concentrated down to dryness on a rotary evaporator; the residue is dissolved in 20 ml of ethyl acetate and purified by flash chromatography (silica gel, 30×5 cm) using petroleum ether/ethyl acetate 2:3. The product fractions and an oxidation byproduct which fluoresces with a blue coloration (methyl 5-(N-benzyloxycarbonyl-1-propin-3-amino-1-yl)uracil-1-acetate) are concentrated to dryness in a rotary evaporator and dried to constant weight under high vacuum.

Product yield: 0.54 9 (45%) of a yellowish solid; R$_f$=0.22 (silica gel, petroleum ether/ethyl acetate 2:3) M.p.: 131–133° C. $^1$H NMR (d$_6$-DMSO, ppm): 11.53 (sb, 1H, NH (uracil)), 7.84 (s, 1H, H—C(6), 7.50 (b, 1H, NH), 7.35 (m, 5H, phenyl), 6.55–6.02 (m, 2H, 2×=CH), 5.04 (s, 2H, CH$_2$Ph), 4.55 (s, 2H, NHC$_2$COO), 3.90–3.64 (m, 2H=CH$_2$), 3.71 (s, 3H, OCH$_3$)

Byproduct yield: 0.38 g R$_f$ (byproduct)=0.3 (silica gel, petroleum ether/ethyl acetate 2:3) $^1$H NMR of the byproduct (d$_6$-DMSO, ppm): 11.41 (sb, 1H, NH (uracil)), 9.14 (db, 1H NH), 7.53 (s, 1H, H—C(6), 7.45–7.19 (m, 5H, phenyl), 5.14 (s, 2H, CH$_2$Ph), 4.54 (s, 2H, NCH$_2$COO), 3.70 (s, 3H, OCH$_3$), 1.79 (D, 2H, CH$_2$NHCOOPH)

EXAMPLE 4

Preparation of 5-(N-benzyloxycarbonylaminoallyl) uracil-1-acetic Acid (Compound 9)

1 g of methyl 5-(N-benzyloxycarbonylaminoallyl)uracil-1-acetate is stirred at room temperature overnight in 20 ml of tetrahydrofuran (THF) and 10 ml of 1 M lithium hydroxide. The THF is then removed on a rotary evaporator. The solution which remains is then diluted with 10 ml of water and adjusted to pH 2 with 2 M hydrochloric acid. It is then extracted three times by shaking with 70 ml of ethyl acetate on each occasion. The combined organic phases are dried over magnesium sulfate, filtered and concentrated to dryness on a rotary evaporator. The brownish solid is dried to constant weight under high vacuum.

Yield: 0.72 g (73%)
R$_f$=0.47 (silica gel, n-butanol/glacial acetic acid/water 4:1:1) M.p.: 168–170° C.
$^1$H NMR (d$_6$-DMSO, ppm): <12 (1H, COOH), 11.47 (sb, 1H, NH (uracil)), 7.83 (s, 1H, H—C (6)), 7.48 (b, 1H, NH), 7.35 (m, 5H, phenyl), 6.53–6.01 (m, 2H, 2×=CH), 5.03 (s, 2H, CH$_2$Ph), 4.42 (s, 2H, NHC$_2$COO), 3.71 (t, 2H, CH$_2$N (allyl))

EXAMPLE 5

Preparation of N-(2-tert-butyloxycarbonylaminoethyl)-N'-5[5-(N-benzyloxycarbonylaminoallyl)uracil-1-ylacetyl] glycine methyl ester 9.36 g of 5-(N-benzyloxycarbonylaminoallyl)uracil-1-acetic acid are dissolved in 10 ml of absolute dimethylformamide (DMF). Freshly activated molecular sieve 4A, 244 μl of diisopropylethylamine and 364 mg of O-(benzotirazol-1-yl)-1,1,3,3-tetramethyluronium hexafluorophosphate (HBTU) are added to the solution. After that, the mixture is stirred at room temperature for 30 min. 159 mg of methyl-N-(2-Boc-aminoethyl)glycinate (K. L. Duoholm et al., Org. Prep. Proc. Int., 1993, 25, 457–461) dissolved in 5 ml of DMF are then added and the mixture is stirred at room temperature for a further 3 hours. After that, the molecular sieve is filtered off and the filtrate is concentrated under high vacuum. The residue is taken up in a little ethyl acetate and the precipitate which forms is filtered off. The filtrate is concentrated down to a volume of approx. 3 ml and is purified by flash chromatography (silica gel, 25×2.5 cm) using petroleum ether/ethyl acetate 1:3 as the eluent. The purified product fractions are concentrated and dried under high vacuum.

Yield: 0.29 g (78%) of colorless crop of crystals; R$_f$=0.76 (silica gel, n-butanol/glacial acetic acid/water 4:2:1)
$^1$H NMR (d$_6$-DMSO, ppm): 11.41 (sb, 1H, NH, (uracil)), 6.92–6.00 (m, 3H, NH, 2×=CH), 5.02 (s, 2H, CH$_2$Ph), 4.71–4.31, 4.06, 3.71 (3×2H, 3×NCH$_2$CO), 3.63 (s, 3H, OCH3), 3.40–3.00 (m, 4H, 2×CH$_2$N)

EXAMPLE 6

Preparation of N-(2-tert-butyloxycarbonylaminoethyl)-N'-[5-N-benzyloxycarbonylaminoallyl)uracil-1-ylacetylglycine (compound 11)

290 mg of N-(2-tert-butyloxycarbonylamino-ethyl)-N'-[N-benzyloxycarbonylaminoallyl)uracil-1-ylacetyl]glycine methyl ester are stirred, at room temperature for 4 hours, in 10 ml of THF and 5 ml of 1 M lithium hydroxide solution. After that, the THF is stripped off on a rotary evaporator. The residue is diluted with 20 ml of water and extracted three times by shaking with 50 ml of ethyl acetate on each occasion. The combined organic phases are dried over magnesium sulfate, filtered, concentrated to dryness on a rotary evaporator and dried under high vacuum.

Yield: 270 mg (97%)
R$_f$=0.67 (silica gel, n-butanol/glacial acetic acid/water 4:2:1) M.p.: 56–159° C.;
UV (MeOH): λ$_{max}$ [nm] (log ε): 238 (4.12), 293 (3.98)
$^1$H NMR (d$_c$-DMSO, ppm): 12.7 (b, 1H, COOH), 11.38/11.36 (2s, 1H, NH, (uracil), 7.63/7.58 (2s, 1H, H—C(6)), 7.44 (m, 1H, NH), 7.35 (m, 5H, phenyl), 6.88/6.69 (2t, 2H, NH), 6.38–6.33/6.11 (m, d, 2H, 2×=CH), 5.02 (s, 2H, CH$_2$Ph), 4.70/4.53 (2s, 2H, NCH$_2$CO), 4.19/3.98 (2s, 2H, NCH$_2$CH), 3.70 (m, 2H, NCH$_2$CO (allyl)9, 3.41–3.03 (m, 4H, 2×CH$_2$N), 1.33/1.37 (2s, 9H, tBu)—rotational isomers, approx. 2:1

EXAMPLE 7

Preparation of Boc-Gly-MBHA support material 2 g of MBHA resin (Novabiochem; 0.56 mmol/g) is left to swell overnight in dichloromethane. After that, it is filtered off with suction and washed with a 5% solution of diisopropylethylamine in N-methyl-pyrrolidone (NMP). After that, 0.77 ml of 0.26 M N-tert-butyloxycarbonyl-(Boc)-glycine in NMP, 0.8 ml of 0.5 M diisopropylethylamine in NMP and 0.96 ml of 0.202 M O-(7-azabenzotriazol-1-yl)-1,1,3,3-tetramethyl-uroniumhexafluorophosphate (HATU) in NMP are added together, preactivated for 2 min and diluted with 5 ml of NMP. The solution is then added to the resin and the mixture is shaken for 2 hours. After that, the resin is filtered off with suction and washed several times with NMP, ethanol and dichloromethane. After that, 10 ml of acetic anhydride/pyridine/NMP 1:2:2 are added to the resin and the mixture is shaken overnight at room temperature (capping). The resin is then filtered off with suction, washed several times with NMP, ethanol and dichloromethane and dried under a high vacuum. A qualitative Kaiser test is negative and indicates quantitative capping. The loading is determined using a quantitative Kaiser test (in accordance with the ABI 433 A synthesizer manual). Loading: 70 μmol/g.

EXAMPLE 8

PNA Synthesis (PNA monomers and labelled monomeric building blocks 11 and 12)

The PNA is synthesized on an Applied Biosystems ABI 433A peptide synthesizer with modified software. The syntheses are carried out in 5 μmol quantities in a 3 ml reaction vessel. A relatively small measuring loop (150 μl) is used. The monomeric building blocks are dissolved in NMP and injected into individual cartridges (140 μl, 0.26 M). The Boc-Gly-derivatized MBHA support material is aliquoted into the 3 ml reaction vessel and installed on the synthesizer. Trifluoroacetic acid/m-cresol 95:5 (2×180 sec); bottle position 2) is used to eliminate the Boc protecting group. In each case, 2 washing modules (dichloromethane module and NMP module in each case consisting of 5 consecutive washing steps) are located between the Boc elimination and the coupling module (dichloromethane=bottle position 9; NMP=bottle position 10). 140 μl of 0.26 M monomer (36 μmol), 150 μl of 0.21 M HATU in NMP (32 μmol) and 150 μl of 0.5 M diisopropylethylamine in NMP (75 μmol) are required in each coupling step (diisopropylethylamine solution=bottle position 7; HATU solution=bottle position 8). The monomers are preactivated (1 min) in the synthesis cartridge and then transferred into the reaction vessel. The coupling time is 10 min, with the monomer concentration during the coupling being 0.08 M. After the coupling module, there comes a capping module containing acetic anhydride/NMP/pyridine 1:25:25 (1 min; bottle position 4). Each synthesis cycle is concluded with an NMP washing module. After the last synthesis cycle, there follows a dichloromethane washing module in order to dry the resin. The couplings of the modified building blocks, in particular, are checked by means of a qualitative Kaiser test.

The PNA is cleaved off the resin, and the protecting groups are eliminated, in a manual step which is performed outside the appliance in a sealable glass frit. The resin is first of all washed with trifluoroacetic acid (TFA) and is then shaken for 1.5 hours with 2 ml of trifluoromethanesulfonic acid/trifluoroacetic acid/m-cresol (2:8:1). The cleavage solution is sucked into a centrifuged tube. Rewashing takes place with 1 ml of trifluoroacetic acid and the PNA is precipitated with diethyl ether. After centrifugation, the precipitate is separated from the supernatant. It is then washed twice with diethyl ether.

The PNAs are analyzed in an analytical RP18 HPLC column (Delta-Pak, Waters, 5μ, 125×4 mm) using a water/acetonitrile/0.1% trifluoroacetic acid gradient (0,2' 100% A, 2-30' 100-60% A, 30-33' 60% A, 33-35' 60-0% A, 35-45' 0%, 45-50' 0-100% A, 50-55' 100% A; A=0.1% TFA in water; B=0.1% TFA in 95% acetonitrile; flow rate 1 ml/min) at 60° C.

The PNAs are purified in a preparative RP18 HPLC column (Nucleosil-RP18/Macherey-Nagel, 5μ, 250×200 mm) using the same elution system (gradient: 0-5' 100% A, 5-40' 100-60% A, 40-45' 60% A, 45-50' 60-0% A, 50-60' 0% A, 60-65' 0-100% A, 65-70' 100% A; A=0.1% TFA in water, B=0.1% TFA in 95% acetonitrile, flow rate 5 ml/min) at 60° C.

The purified PNAs are analyzed by mass spectrometry using MALDITOF MS.

EXAMPLE 9

PNA Synthesis and Oligonucleotide Synthesis 9.1 PNA Synthesis Using Building Block 11 and Post-labeling with the N-hydroxysuccinimide Ester of Ru(bipyridyl)$_3$ Acid PNA 20 is prepared by the above-described synthesis method (Example 8) using building block 11 as the coupling building block at position 12. After the synthesis cycle has come to an end, the terminal Boc protecting group is eliminated with TFA/m-cresol 95:5 (180 sec.). After that, the resin is washed with consecutive NMP and dichloromethane washing steps. The terminal amino function is then acetylated with acetic anhydride/pyridine/NMP 1:2:2 (1 hour). The capping solution is then sucked off and washing takes place with NMP and dichloromethane. The PNA is cleaved off and purified by HPLC as described above (Example 8). MALDITOF-MS: 5545.9 (Δ 0.005%).

A 43 OD$_{260}$ aliquot of the purified PNA is concentrated to dryness. The PNA is then dissolved in 0.1 M NaHCO$_3$ buffer, pH 8.5 (1 ml). The pH is checked and readjusted where appropriate. After that, 2 mg of the N-hydroxysuccinimide ester of Ru(bipyridyl)$_3$ acid (Boehringer Mannheim, Ident. No. 171 74 64), dissolved in 1 ml of DMSO, are added and the mixture is shaken overnight in order to label the exposed amino function of the incorporated building block 11. After that, the PNA is dialyzed against water (1000 MWCO, SpectraPor 6). The mixture is then concentrated to dryness and the residue is purified in a preparative RP 18 HPLC column (Nucleosil-RP18/Macherey-Nagel, 5μ, 250×20 mm) (gradient: 0-5' 80% A, 5-30' 80-60% A, 30-35' 60% A, 35-65' 60-0% A, 65-70' 0% A, 70-75' 0-100% A, A: 0.1% TFA in water, B: 0.1% TFA in 95% acetonitrile, flow rate: 4 ml/min.

Yield: 18 OD$_{260}$MS (MALDITOF: 6201.8 (Δ 0.02%).

9.2 PNA Synthesis Using Building Block 12 and Post-labeling with the N-hydroxysuccinimide Ester of Ru(bipyridyl)$_3$ Acid Building block 12 is synthesized as described in G. Haaima et al., Angew. Chem., 1996, 108, 2068–2070.

PNA 21 is prepared by the above-described synthesis method (Example 8) using building block 12 as the twelfth coupling building block (5 μmol scale).

Yield: 114 OD$_{260}$

MS (MALDITOF): 6228.0 (Δ 0.02%).

9.3 Synthesized PNA Molecules

The following PNA molecules are prepared. The sequence is derived from a Chlamydia probe (possessing the base nucleotide sequence given in SEQ ID NO. 1, as shown in 15):

H-CAT AGC ACT ATA GAA CTC TG Gly-NH$_2$ 15 (SEQ ID NO: 1)

Bio (Ado)$_3$ CAT AGC ACT ATA GAA CTC TG Gly-NH$_2$ 17

Ru Ado CAT AGC ACT ATA GAA CTC TG Gly-NH$_2$ 19

Ac-CAT AGC AC(Ru-U) ATA GAA CTC TG Gly-NH$_2$ 20

Ac-CAT AGC AC (T$_{Lys-Ru}$) ATA GAA CTC TG Gly-NH$_2$ 21

Ru Ado CAT AGC AC(Ru-U) ATA GAA CTC TG Gly-NH$_2$ 23

Ru Ado CAT AGC ACT ATA GAA C(Ru-U)C TG Gly-NH$_2$ 25

(Ru-Lys) (Ru-Lys) CAT AGC ACT ATA GAA CTC TG Gly-NH$_2$ 26

(Ru-Lys) (Ru-Lys) CAT AGC ACT ATA GAA CTC TG Gly-NH$_2$ 27

In the sequences, Ru-U is the incorporated building block 11, which has been post-labelled with Ru(bpy)$_3$-OSu on the amino function on uracil C-5. $T_{Lys-Ru}$ is the incorporated building block 12, which has been post-labelled with Ru(bpy)$_3$-OSu on the amino function of the lysine in the backbone. Ru-Lys, Ru, Bio and Ado have the meanings depicted in FIG. 4.

9.4 Synthesized Oligonucleotides

The following oligonucleotides (possessing the base nucleotide sequence given in SEQ ID NO. 2, as shown in 13, or that given in SEQ ID NO. 1, as shown in 14) are synthesized, as reference or counterstrands, using the standard phosphoramidite method:

5'-CAG AGT TCT ATA GTG CTA TG-3' 13 (SEQ ID NO: 2)

5'-CAT AGC ACT ATA GAA CTC TG 3' 14 (SEQ ID NO: 3)

5'-Bio CAT AGC ACT ATA GAA CTC TG 3' 16 (SEQ ID NO: 4)

5'-Ru CAT AGC ACT ATA GAA CTC TG 3' 18 (SEQ ID NO: 5)

5'-Ru CAT AGC AC(Ru-U) ATA GAA CTC TG 3' 22 (SEQ ID NO: 6)

5'-Ru CAT AGC ACT ATA GAA C(Ru-U)C TG 3' 24 (SEQ ID NO: 7)

In the sequences, Ru-U is the incorporated DNA analog of building block 11, which has been post-labelled with Ru(bpy)$_3$-OSu on the amino function on uracil C-5. The 5'-terminal Ru and Bio are in each case coupled by way of the corresponding phosphoramidite derivative.

EXAMPLE 10

Determining the Melting Temperatures 10.1 Methodology

The melting temperatures of hybrids formed from two complementary oligomers are determined in a Kontron Uvikon 931 spectrophotometer. The temperature in the cuvette blocks is controlled using a Haake DC5 heating/cooling thermostat, while internal $T_m$ is monitored in a cuvette using a PD10 thermoindicator. Kontron $T_m$ software is used. Measurements are carried out in 0.5° C. steps in 100 mM NaCl, 10 mM Na phosphate, 0.1 mM EDTA, pH 7, as the melting curve buffer. Both oligomers are employed in equimolar quantities. The final oligomer concentration is 2.5 nmol/ml.

10.2 Results

Tm experiments are carried out in order to investigate the influence of the label or of the label position and to compare the stability of DNA-DNA and PNA-DNA duplexes. The Tm values are summarized in Tab. 1. The Tm of the DNA-DNA duplex is 56° C. While 5'-biotinylation has virtually no effect on the Tm (55.9° C.), 5'-ruthenylation leads to a Tm, which has been slightly increased by 0.7° C., of 56.7° C. The same picture is found with the DNA-PNA duplex. The unlabelled PNA-DNA duplex has a Tm of 73.5° C., while aminoterminal biotinylation of the PNA has no effect on stability (73.5° C.), and amino terminal rutheny-lation leads, in this case as well, to an 0.7° C. increase in stability, i.e. to 74.2° C.

Labeling with Ru on an internal Lys amino function (building block 12) yields the same 0.7° C. gain in stability, to 74.2° C., as is obtained when Ru is incorporated amino-terminally. Labeling with Ru internally at the C-5 position of the uracil (building block 11) in fact leads to the highest stabilization of 1.5° C., i.e. to 75.0° C. The observation was then also surprising that, while labeling internally with Ru at the C-5 position of the uracil base leads to a slight destabilization of the double strand in DNA-DNA duplexes, analogous internal labeling of the PNA results in stabilization of the PNA-DNA duplex. This is shown by the following comparison of the doubly ruthenylated derivatives (Tm experiment 9 compared with 10 and 11 with 12): whereas the DNA duplex is destabilized, as compared with the 5'-Ru labeling and depending on the position of the 2nd Ru labeling, by 2.3° C., to 54.4° C., and by 1.2° C., to 55.3° C., respectively, the analogous insertion of the 2nd Ru label into the PNA, by way of building block 11, and in addition to the aminoterminal Ru labeling, results in a stabilization by 2.3° C., to 76.5° C., and in an unaltered Tm of 74.2° C., respectively. Double aminoterminal Ru labeling with Ru-Lys likewise leads to a stabilization of the PNA-DNA duplex of 2.3° C., as compared with single Ru labeling, i.e. to 76.5° C. If the terminal Ru labels are separated by an Ado linker, the stabilization is somewhat lower (1.5° C.).

Tab. 1: Tm Experiments

| Experiment | DNA/PNA | Conc. OD/ml | Vol. µl | 10 × buffer µl | Water µl | Tm |
|---|---|---|---|---|---|---|
| 1 | DNA 13 | 26.2 | 9.50 | 100 | | 56.0 |
| | DNA 14 | 24.8 | 10.00 | | 880 | |
| 2 | DNA 13 | 26.2 | 9.50 | 100 | | 55.9 |
| | 5'-Bio-DNA 16 | 30.9 | 8.00 | | 882 | |
| 3 | DNA 13 | 26.2 | 9.50 | 100 | | 56.7 |
| | 5'-Ru-DNA 18 | 10.2 | 24.50 | | 866 | |
| 4 | DNA 13 | 26.2 | 9.50 | 100 | | 73.5 |
| | PNA 15 | 73.2 | 3.40 | | 887 | |
| 5 | DNA 13 | 26.2 | 9.50 | 100 | | 73.5 |
| | 5'-Bio-PNA 17 | 16.7 | 15.00 | | 875 | |
| 6 | DNA 13 | 26.2 | 9.50 | 100 | | 74.2 |
| | 5'-Ru-PNA 19 | 15.1 | 16.50 | | 874 | |
| 7 | DNA 13 | 26.2 | 9.50 | 100 | | 75.0 |
| | U-Ru-PNA 20 | 6.2 | 40.30 | | 850 | |
| 8 | DNA 13 | 26.2 | 9.50 | 100 | | 74.2 |
| | Lys-Ru-PNA 21 | 56.8 | 4.40 | | 886 | |
| 9 | DNA 13 | 26.2 | 9.50 | 100 | | 54.4 |
| | 5'-Ru-U-Ru-DNA 22 | 6.5 | 38.50 | | 852 | |
| 10 | DNA 13 | 26.2 | 9.50 | 100 | | 76.5 |
| | 5'-Ru-U-Ru-PNA 23 | 15.4 | 16.20 | | 874 | |
| 11 | DNA 13 | 26.2 | 9.50 | 100 | | 55.3 |
| | 5'-Ru-U-Ru-DNA 24 | 4.5 | 55.50 | | 835 | |
| 12 | DNA 13 | 26.2 | 9.50 | 100 | | 74.2 |
| | 5'-Ru-U-Ru-PNA 26 | 7.2 | 34.70 | | 856 | |
| 13 | DNA 13 | 26.2 | 9.50 | 100 | | 76.5 |
| | 5' 2Xru-Lys-PNA 26 | 30.5 | 8.20 | | 882 | |
| 14 | DNA 13 | 26.2 | 9.50 | 100 | | 75.7 |
| | 5'-Ru-Lys-Ado-Ru-PNA 27 | 19.1 | 13.00 | | 877 | |

What is claimed is:

1. Compound of the formula (I)

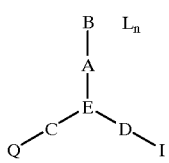

(I)

in which:

B is a natural or unnatural nitrogen base which optionally carries a protecting group, L is a labeling group with the labeling group being ruthenium (bipyridyl)$_3$ bonded to B, A, C and D are in each case, independently of each other, chemical bonds or organic radicals, E is a group which is selected from N, $R^1N^+$ or CH, where $R^1$ is an organic radical or hydrogen, Q is a group $NR^2Y$, where $R^2$ is an organic radical or hydrogen, and Y is a protecting group or a carrier, I is a group which is selected from COX, CSX, SOX or $SO_2X$, where X is OH, SH, OM, SM or a protecting group, M is a cation, and n is an integer from 1 to 3.

2. A compound as claimed in claim 1,
wherein
B is a nitrogen base selected from thymine, uracil, cytosine, adenine, guanine, hypoxanthine, purine, 7-deazapurine, 2,4-diaminopurine, 2,6-diaminopurine, 7-deazaguanine, pseudouracil, pseudocytosine, pseudoisocytosine, $N_4,N^4$-ethanocytosine, $N^6,N^6$-ethano-2,6-diaminopurine, 5-($C_3$–$C_6$)-alkynylcytosine, 5-fluorouracil and 2-hydroxy-5-methyl-4-triazolopyrimidine, with the nitrogen base optionally carrying a protecting group.

3. A compound as claimed in claim 1,
wherein
the nitrogen base is a pyrimidine base and the group L is bonded to the C-5 position.

4. A compound as claimed in claim 1, wherein the nitrogen base is cytosine, pseudocytosine, pseudoisocytosine, $N^4,N^4$-ethanocytosine or 5-($C_3$–$C_6$)-alkynylcytosine, and the group L is bonded to the N4 position of the nitrogen base.

5. A compound as claimed in claim 1, wherein the nitrogen base is a purine base and the group L is bonded to the C-8 position of the nitrogen base.

6. A compound as claimed in claim 1, wherein the nitrogen base is adenine, 7-deazaadenine, 2,4-diaminoadenine, 2,6-diaminoadenine or $N^6,N^6$-ethano-2,6-diaminoadenine, and the group L is bonded to the N-6 position of the nitrogen base.

7. A compound as claimed in claim 1, wherein the nitrogen base is guanine or 7-deazaguanine, and the group L is bonded to the N-2 position of the nitrogen base.

8. A compound as claimed in claim 1 or 2, wherein the nitrogen base is a 7-deazapurine and the group L is bonded to the C-7 position.

9. A compound as claimed in claim 1, wherein

A is a $C_1$–$C_{10}$-alkylene, alkenylene or alkynylene radical which optionally contains heteroatoms and/or substituents.

10. A compound as claimed in claim 9, wherein

A is a —$CH_2$—CO— radical.

11. A compound as claimed in claim 1, wherein

C is a $C_1$–$C_{10}$-alkylene, alkenylene or alkynylene radical which optionally carries heteroatoms and/or substituents.

12. A compound as claimed in claim 11, wherein

C is a —$(CH_2)_2$— radical.

13. A compound as claimed in claim 1, wherein

D is a $C_1$–$C_{10}$-alkylene, alkenylene or alkynylene radical which optionally carries heteroatoms and/or substituents.

14. A compound as claimed in claim 13, wherein

D is a —$CH_2$— radical.

15. A compound as claimed in claim 1, wherein

A and B or A and D form a ring structure.

16. A method of synthesizing nucleic acid-binding peptide oligomers comprising using the compounds of formula (I) as claimed in claim 1 as monomeric building blocks.

17. A nucleic acid-binding oligomer, which contains at least one monomeric building block having a labeling group as defined in claim 1 which is coupled to a nitrogen base and/or to a peptide backbone.

18. An oligomer as claimed in claim 17, which contains at least one monomeric building block which is selected from compounds of the formulae (I) and (II).

19. An oligomer as claimed in claim 17, wherein, when hybridizing with a complementary nucleic acid, either (1) the resulting hybrid has a higher melting point than does a hybrid which contains an oligomer without a labeling group, or (2) the destabilization is weaker in a PNA-nucleic acid hybrid than in a nucleic acid-nucleic acid hybrid.

20. An oligomer as claimed in claim 17, which contains several identical or different labeling groups.

21. An oligomer as claimed in claim 17, which is additionally coupled to labeling groups at the N terminus and/or the C terminus.

22. A nucleic acid-binding oligomer which has a structure of the general formula (III):

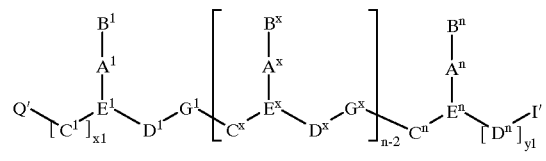

(III)

in which:

n is an integer of at least 3, x is an integer from 2 to n−1, each of the groups $B^1$ to $B^n$ is a nitrogen base as previously defined, each of the groups $C^1$–$C^n$ has the meaning $(CR^6R^7)_y$, where $R^6$ is hydrogen and $R^7$ is selected from the group consisting of the side chains of naturally occurring alpha-amino acids, or $R^6$ and $R^7$ are independently selected from the group consisting of hydrogen, $C_1$–$C_6$-alkyl, aryl, aralkyl, heteroaryl, hydroxyl, $C_1$–$C_6$-alkoxy, $C_1$–$C_6$-alkylthio, $NR^3R^4$ and $SR^5$, where $R^3$ and $R^4$ are as defined below and $R^5$ is hydrogen, $C_1$–$C_6$-alkyl or $C_1$–$C_6$-alkyl which is substituted by hydroxyl, $C_1$–$C_6$-alkoxy or $C_1$–$C_6$-alkylthio, or $R^6$ and $R^7$ together form an alicyclic system or heterocyclic system, or $C^1$–$C^n$ is CO, CS or $CNR^3$;

each of the radicals $D^1$–$D^n$ has the meaning $(CR^6R^7)_z$, where $R^6$ and $R^7$ are as defined before, and y and z are integers of from 0 to 10, where the sum of y+z is at least 2;

each of the radicals $G^1$–$G^{n-1}$ has the meaning —$NR^3CO$, $NR^3CS$—, —$NR^3$—SO— or —$NR^3SO_2$ in any orientation, where $R^3$ is as defined below;

each of the radicals $A^1$–$A^n$ and $E^1$–$E^n$ is selected such that:

(a) $A^1$–$A^n$ is a group of the formula (IIIa), (IIIb), (IIIc) or (IIId), and $E^1$–$E^n$ is N or $R^3N^+$, or (b) $A^1$–$A^n$ is a group of the formula (IIId), and $E^1$–$E^n$ is CH:

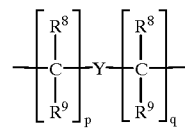

(IIIa)

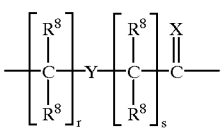

(IIIb)

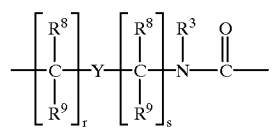

(IIIc)

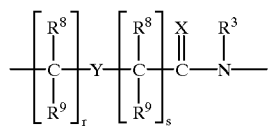

in which:
X is O, S, Se, NR$^3$, CH$_2$ or C(CH$_3$)$_2$,
Y is a single bond, O, S or NR$^4$,
p and q are in each case an integer of from 0 to 5,
r and s are in each case integers of from 0 to 5,
each of the radicals R$^8$ and R$^9$ is selected independently from the group consisting of hydrogen, hydroxyl, amine, halogen, C$_1$–C$_4$-alkoxy, C$_1$–C$_4$-alkylthio and unsubstituted or substituted C$_1$–C$_4$-alkyl, where the substituents are selected from hydroxyl, C$_1$–C$_4$-alkoxy or C$_1$–C$_4$-alkylthio groups;
each of the radicals R$^3$ and R$^4$ is selected independently from the group consisting of hydrogen, C$_1$–C$_4$-alkyl which is unsubstituted or substituted by hydroxyl or C$_1$–C$_4$-alkoxy or C$_1$–C$_4$-alkylthio, hyroxyl, C$_1$–C$_6$-alkoxy, C$_1$–C$_6$-alkylthio and amine;
Q' and I' are selected independently from the group consisting of NH$_2$, CONH$_2$, COOH, hydrogen, C$_1$–C$_6$-alkyl, O(C$_1$–C$_6$)-alkyl, an amine which is blocked by a protecting group, labeling groups, intercalators, chelators, peptides, proteins, carbohydrates, lipids, steroids, nucleosides, nucleotides, nucleoside-diphosphates, nucleosidetriphosphates, oligonucleotides, including oligoribonucleotides and oligodeoxyribonucleotides, oligonucleosides and soluble and insoluble polymers and also nucleic acid-binding groups, and
X$^1$ and Y$^1$ is in each case an integer of from 0 to 10, with the compound being such that ruthenium (bipyridyl)$_3$ is present at at least one nitrogen base and/or at a position in the peptide backbone.

23. An oligomer as claimed in claim 22,
which
possesses at least one monomeric building block of the general formula (IV)

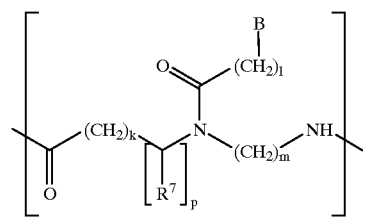

in which:
B is a nitrogen base as previously defined, k, l and m are, independently, an integer from 0 to 5,
p is 0 or 1, and
R$^7$ is selected from the group consisting of hydrogen and the side chains of naturally occurring alpha-amino acids.

24. A method of labeling a biological substance, comprising the step of binding the oligomer as claimed in claim 17 to the biological substance.

25. A reagent for hybridizing with nucleic acids, which contains a nucleic acid-binding oligomer as claimed in claim 17.

26. A reagent kit for hybridizing nucleic acids, which contains a reagent as claimed in claim 25 in addition to other test components.

27. The method as claimed in claim 24, wherein the biological substance is a nucleic acid and wherein the oligomer is hybridized with the nucleic acid.

28. The method as claimed in claim 27 for isolating the nucleic acid, said method further comprising separating at least one oligomer bound to the nucleic acid from any free oligomer to isolate the nucleic acid.

29. The nucleic acid-binding oligomer as claimed in claim 22, wherein each of the groups C$^1$–C$^n$ is CR$^6$R$^7$, CHR$^6$CHR$^7$ or CR$^6$R$^7$CH$_2$.

30. The nucleic acid-binding oligomer as claimed in claim 22, wherein each of the radicals D$^1$–D$^n$ is CR$^6$R$^7$, CHR$^6$CHR$^7$ or CH$^2$CR$^6$CR$^7$.

31. The nucleic acid-binding oligomer as claimed in claim 22, wherein the sum of y+z is more than 2 but not more than 10.

32. The nucleic acid-binding oligomer as claimed in claim 22, wherein the sum of p+q is 5 or less.

33. The nucleic acid-binding oligomer as claimed in claim 22, wherein the sum r+s is 5 or less.

34. A reagent kit for hybridizing nucleic acids, which comprises a reagent as aimed in claim 25.

35. The method as claimed in claim 27 for detecting the nucleic acid, said method further comprising detecting at least one oligomer bound to the nucleic acid to indicate the presence of the nucleic acid.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: The nucleotide sequence of a Chlamydia probe

<400> SEQUENCE: 1
catagcacta tagaactctg                                               20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: The nucleotide sequence of a reference or
      counterstrand probe to the sequence  shown in SEQ ID No. 1

<400> SEQUENCE: 2
cagagttcta tagtgctatg                                               20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthesized oligonucleotide

<400> SEQUENCE: 3
catagcacta tagaactctg                                               20

<210> SEQ ID NO 4
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthesized oligonucleotide
<221> NAME/KEY: modified_base
<222> LOCATION: (1)..(1)
<223> OTHER INFORMATION: Base is modified by Bio

<400> SEQUENCE: 4
ccatagcact atagaactct g                                             21

<210> SEQ ID NO 5
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthesized oligonucleotide
<221> NAME/KEY: modified_base
<222> LOCATION: (1)..(1)
<223> OTHER INFORMATION: Base is modified by Ru

<400> SEQUENCE: 5

-continued

```
ccatagcact atagaactct g                                      21

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthesized oligonucleotide
<221> NAME/KEY: modified_base
<222> LOCATION: (1)..(1)
<223> OTHER INFORMATION: Base modified by Ru
<221> NAME/KEY: modified_base
<222> LOCATION: (10)..(10)
<223> OTHER INFORMATION: Base modified by Ru

<400> SEQUENCE: 6
ccatagcacu atagaactct g                                      21

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthesized oligonucleotide
<221> NAME/KEY: modified_base
<222> LOCATION: (1)..(1)
<223> OTHER INFORMATION: Base modified by Ru
<221> NAME/KEY: modified_base
<222> LOCATION: (18)..(18)
<223> OTHER INFORMATION: Base modified by Ru

<400> SEQUENCE: 7
catagcacta tagaacuctg                                        20
```